(12) United States Patent
Hoijer et al.

(10) Patent No.: US 9,497,984 B2
(45) Date of Patent: Nov. 22, 2016

(54) NUTRITIONAL TABLET

(71) Applicant: N.V. Nutricia, Zoetermeer (NL)

(72) Inventors: Maarten Anne Hoijer, Wageningen (NL); Anneke Maria Fransiska Olde Riekerink, Oldenzaal (NL)

(73) Assignee: N.V. Nutricia, Zoetermeer (NL)

(*) Notice: Subject to any disclaimer, the term of this patent is extended or adjusted under 35 U.S.C. 154(b) by 0 days.

(21) Appl. No.: 14/189,254

(22) Filed: Feb. 25, 2014

(65) Prior Publication Data
US 2014/0287089 A1 Sep. 25, 2014

Related U.S. Application Data

(63) Continuation of application No. 13/499,230, filed as application No. PCT/NL2011/050866 on Dec. 20, 2011, now abandoned.

(30) Foreign Application Priority Data

Dec. 24, 2010 (WO) .............. PCT/NL2010/050889

(51) Int. Cl.
*A23L 1/29* (2006.01)
*A23L 1/308* (2006.01)
*A23C 9/18* (2006.01)
*A23L 1/30* (2006.01)

(52) U.S. Cl.
CPC ............ *A23L 1/308* (2013.01); *A23C 9/18* (2013.01); *A23L 1/296* (2013.01); *A23L 1/3006* (2013.01)

(58) Field of Classification Search
CPC .......... A23C 9/18; A23C 9/203; A23L 1/308; A23L 1/296
See application file for complete search history.

(56) References Cited

U.S. PATENT DOCUMENTS

| | | |
|---|---|---|
| 3,241,975 A | 3/1966 | Brochner |
| 2004/0101596 A1 | 5/2004 | Ndife et al. |
| 2004/0228903 A1 | 11/2004 | Te Hennepe et al. |
| 2009/0162489 A1 | 6/2009 | Singh |
| 2010/0317573 A1 | 12/2010 | Goedhart et al. |
| 2011/0097401 A1 | 4/2011 | Phillips et al. |

FOREIGN PATENT DOCUMENTS

| | | |
|---|---|---|
| CN | 1559244 | 1/2005 |
| EP | 0 609 064 A1 | 8/1994 |
| EP | 1 048 216 A1 | 11/2000 |
| EP | 1 769 682 A1 | 4/2007 |
| EP | 1 795 204 A1 | 6/2007 |
| EP | 2 090 175 A1 | 8/2009 |
| JP | 08-116883 A | 5/1996 |
| WO | WO-98/50054 A1 | 11/1998 |
| WO | WO-01/17503 A2 | 3/2001 |

(Continued)

OTHER PUBLICATIONS

Derwent-ACC-No. 2009-A33080, Derwent week: 200901, "Solid pharmaceutical formulation for infants", Dec. 11, 2008, pp. 1-5.*

(Continued)

*Primary Examiner* — Helen F Heggestad
(74) *Attorney, Agent, or Firm* — Foley & Lardner LLP; Sunit Talapatra

(57) ABSTRACT

To improve the solubility and the speed of dissolution of nutritional tablets comprising protein, fat and carbohydrates, dietary fibers are included in the nutritional tablets.

14 Claims, 1 Drawing Sheet

(56) References Cited

FOREIGN PATENT DOCUMENTS

| WO | WO-2006/022543 A1 | 3/2006 |
|----|-------------------|--------|
| WO | WO-2009/121839 A1 | 10/2009 |
| WO | WO-2012/080469 A1 | 6/2012 |

OTHER PUBLICATIONS

"Approval of using the sign that relates to specific food," SyokuAn Minister of Health, Labor & Welfare, Jun. 26, 1997, with partial English translation, 15 pgs.
Bhowmik, D. et al., "Fast Dissolving Tablet: An Overview," Journal of Chemical and Pharmaceutical Research, 2009, vol. 1, No. 1, pp. 163-177.
Package of the infant formula "Hohoemi Cube" of Meiji, 2009, with partial translation.
Declaration by Mitsuho Shibata, 1 pg.
Emcosoy—product information; http://www.jrspharma.de/Pharma/wDeutsch/produktinfo/productinfo_emcosoy.shtml , 2 pgs.
English translation of the list of ingredients of the infant formula "Hohoemi Cube", 1 pg.
Experimental Results of the solubility and the hardness measurement of the "Hohoemi Cube", 1 pg.
Foodbev.com/diary—Issue 32—Aug.-Sep. 2010, 6 pgs.
Http://www.chemopharma.com/images/mingtai/Comprecel.pdf, 6 pgs.
International Search Report for PCT/NL2011/050866—mailed Mar. 5, 2012.
Kasetsart, j. "Optimization of Supplementary Protein Milk Tablet Formulation for Rural School Children under Her Royal Highness Princess Maha Chakri Sirindhom's Project," Nat. Science, vol. 41, 2007, pp. 733-739.
Results of the hardness measurement of the "Hohoemi Cube", 1 pg.
Written Opinion for PCT/NL2011/050866—mailed Mar. 5, 2012.
Manual English translation of paragraph [0007] of JP 08-116883 A.
Manual English translation of paragraph [0007] of JP 08-116883 A (published May 14, 1996) created on Jan. 20, 2016.

* cited by examiner

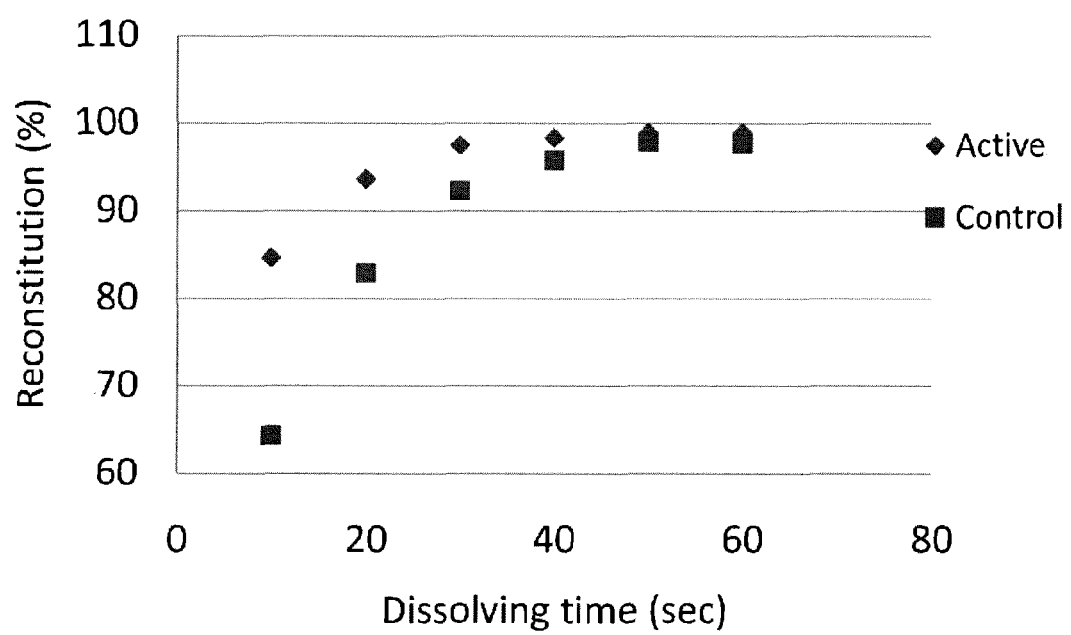

NUTRITIONAL TABLET

CROSS-REFERENCE TO RELATED APPLICATIONS

This application is a continuation application of U.S. application Ser. No. 13/499,230, which was filed as a National Phase of International Patent Application No. PCT/NL2011/050866, filed Dec. 20, 2011, published as WO 2012/087122, which claims priority to International Patent Application No. PCT/NL2010/050889, filed Dec. 24, 2010. The contents of these applications are herein incorporated by reference in their entirety.

FIELD OF THE INVENTION

The present invention is in the field of nutrition in solid form, which is for drinking upon dissolution.

BACKGROUND OF THE INVENTION

Nutrition in solid form, in particular in the form of a tablet, has the advantage of being easy in use by the consumers. For example in preparing infant milk formulae the scooping of powders is difficult potentially leading to dosing mistakes and/or to spilling of the powder. Therefore there is a need for tablets for nutritional formulae that are not in a ready to feed format. Since tablets are also a convenience product, the tablets should be convenient for use. This means that the tablets should be strong enough to be transported in a box or flow wrap and handled by the consumer, while at the same time the tablets should dissolve quick enough, i.e. comparable with the corresponding powder formulae. When preparing a tablet with a nutritional composition, the problem is to strike the balance between the hardness and friability of the tablet and the solubility of the tablet.

In the art when looking at tablets in general, dissolution rate has been addressed by using an effervescent system e.g. bicarbonate that helps to dissolve the tablet quickly. However, such systems cannot be used in food compositions since this would lead to lots of practical issues like foam formation, increase in salt content, etc. Other approaches use specific powder features like loose density, and specific free fat content and compressing circumstances. Drawbacks are in the significantly limited processing possibilities for making tablets, potentially leading to increased cost price.

EP 1048216 discloses tablets including tablets based on infant formula.

EP 1769682 discloses tablets with a specific porosity and free fat content wherein the tablets contain dairy proteins.

U.S. Pat. No. 3,241,975 disclosing tablets prepared from dairy products

The inventors of the present invention therefore tried to find an alternative for preparing a nutritional tablet.

SUMMARY OF THE INVENTION

It is known in the art that it is difficult to make a tablet comprising a nutritional composition comprising dairy protein and fat. The present inventors when making compressed infant formula and medical foods in the form of tablets were challenged with the problem that the tablets need to dissolve quickly and completely, while on the other hand the tablets should be hard enough, with a high breaking strength, to withstand normal handling in a package or flow wrap without falling apart or breaking. Thus when preparing a tablet with a nutritional composition, especially comprising as main ingredients protein, fat and carbohydrates, the problem is to find the balance between the strength of the tablet and the solubility of the tablet.

Surprisingly the inventors found that dietary fibers can be used as a nutritionally acceptable ingredient to improve the solubility and the speed of dissolution of nutritional tablets comprising protein, fat and carbohydrates. Thus when dietary fibers are used for preparing nutritional compositions in tablet form, the solubility of the tablet is improved while having a sufficient hardness.

DETAILED DESCRIPTION OF THE INVENTION

The invention thus concerns a composition comprising fat, protein and carbohydrates, wherein the carbohydrates comprise dietary fibers, and wherein the composition is compressed in the form of a tablet with a hardness of 15 N to 250 N when tested in a hardness tester wherein a force is applied horizontally on the tablet with a constant test speed of 2 mm/s. Hereafter, this is also referred to as the (present) composition in the form of a tablet.

In the representative example 1 it can be seen that the formula prepared with dietary fibers have in improved solubility when compared to exactly the same formula wherein the dietary fibers are absent.

Also other examples showed that dietary fibers improve the solubility of compressed powders.

In a preferred embodiment the composition in the form of a tablet according to the present invention comprises protein, fat and carbohydrates wherein the carbohydrates comprise at least 1 weight percent (wt %) dietary fibers based on the total weight of the composition. Preferably the composition in the form of a tablet comprises dietary fibers in a range between 1 and 15 wt % of the total composition.

As mentioned before, especially for infant formula, where parents are used to dissolve powder products for preparing a bottle of formula, the dissolution time is very important and is preferably be in the range similar to the powder product. Preferably the dissolution time is not longer than 60 seconds upon shaking. Therefore the present invention is particularly preferred for nutritional formulae and in particular for preparing an infant formula in tablet form or a medical food in tablet form. In one embodiment, the composition in the form of a tablet according to the present invention is an infant formula. In one embodiment, the composition in the form of a tablet according to the present invention is a medical food.

The present invention also concerns the use of the present composition in the form of a tablet for the dietary management of growth in infants between 0 and 36 months. This can also be worded as a method for the dietary management of growth in infants between 0 and 36 months, comprising administering the present composition in the form of a tablet. Also this can be worded as the present composition in the form of a tablet for use in the dietary management of growth in infants between 0 and 36 months. The invention cal also be worded as the use of a composition comprising fat, protein and carbohydrates, wherein the carbohydrates comprise dietary fibers for the preparation of a nutritional composition in the form of a tablet with a hardness of 15 N to 250 N when tested in a hardness tester wherein a force is applied horizontally on the tablet with a constant test speed of 2 mm/s, for use in the dietary management of growth in infants between 0 and 36 months.

The invention also concerns the use of dietary fibers for improving the dissolving time of compressed powders comprising fat, protein and carbohydrates, wherein the carbohydrates comprise the dietary fibers in a range between 1 and 15 wt % of the total composition.

Hardness or Breaking Strength

The standard method used for testing hardness of a tablet is compression. The tablet is placed between two jaws that crush the tablet. The force applied to the tablet is measured and it is detected when the tablet fractures. Preferably a tablet according to the present invention has a hardness between 15 N and 250 N using a Schleuniger hardness tester. The tablets are placed horizontally on the holder of the Schleuniger hardness tester and a force is applied horizontally on the tablet with a constant test speed of 2 mm/s. In a preferred embodiment the tablet comprises at least 1 wt % dietary fiber and has a hardness in the range of 20 N to 250 N. Since the use of dietary fibers shortens the dissolving time harder tablets can be made. Harder tablets are preferred since they are more stable during transport and handling of the tablets. A more preferred hardness of the tablets is therefore in the range of 25 N to 250 N, and even more preferred 30 N to 250 N when tested in a hardness tester wherein a force is applied horizontally on the tablet with a constant test speed of 2 mm/s.

Methods for preparing tablets are known per se. The composition in the form of a tablet according to the present invention is preferably prepared by compressing a powder. It is routine practice for one skilled on the art to prepare tablets by compressing powder, taking into account the desired strength of the tablet in relation to the degree of compression.

Dietary Fiber

According to the present invention not all sugars are capable of improving the solubility of the compressed nutritional powders. As can be seen from example 1 wherein the infant milk formula with GOS and IcFOS is compared with the exact same product comprising lactose. From this experiment it can be seen that dietary fibers GOS and IcFOS can improve the dissolving time of the tablet. Preferably the present composition comprises at least one dietary fibre selected from the group consisting of galactooligosaccharides, trans galactooligosaccha rides, fructans, fructooligosaccharides, long chain fructooligosaccharides (IcFOS, e.g. inulin), short chain fructooligosaccharides (scFOS), xylooligosaccharides, palatinoseoligosaccharide, soybean oligosaccharide, pectin, pectate, alginate, sialoglycans, fucoidan, fucooligosaccharides, and/or degradation products of dietary fibres. More preferably the composition according to the present invention comprises a mixture of galactooligosaccharide and fructans.

Protein

The present composition in the form of a tablet comprises protein. Any protein can be used in the composition in the form of a tablet according to the present invention. Vegetable protein, animal protein or mixtures thereof are equally effective. A preferred protein is however whey protein in an amount of at least 20 wt %, more preferably 50 wt % based on total weight of protein, even more preferably at least 55 weight percent (wt %) and even more preferably between 55 and 75 wt % based on total weight of protein. Protein includes all nitrogen sources such as free amino acids, hydrolysates and intact protein.

In a preferred embodiment of the invention the composition in the form of a tablet comprises a relatively high amount of protein, preferably at least 8% based on total calories, more preferably between 8 and 70% based on total calories of the composition in the form of a tablet is from protein. In a most preferred embodiment the protein is a fast absorbing protein such as bovine whey protein, or protein hydrolysates. The present composition in the form of a tablet preferably comprises 7 to 25 wt. % protein, more preferably 8 to 10 wt. %.

Nutritional Compositions

Infant Formula in Tablet Form

The term infant formula according to the present invention is meant to include growing up milks and follow on formula for providing the complete daily nutritional requirements to a human subject with an age below 36 months, more preferably a human infant.

The present composition in the form of a tablet is a nutritional composition and preferably comprises digestible carbohydrate. Preferred digestible carbohydrates are lactose, glucose, sucrose, fructose, galactose, maltose, starch and maltodextrin. Lactose is the main digestible carbohydrate present in human milk. The present composition in the form of a tablet preferably comprises lactose. The present composition in the form of a tablet preferably comprises 30 to 70 wt. %, more preferably 40 to 65 wt. % digestible carbohydrates. The present nutritional composition in the form of a tablet preferably comprises digestible carbohydrate, wherein at least 35 wt. %, more preferably at least 50 wt. %, more preferably at least 70 wt. %, of the digestible carbohydrate is lactose. The present composition in the form of a tablet preferably comprises at least 30 wt. % lactose, preferably at least 40 wt. %. Based on total calories the composition preferably comprises 30 to 60% calories derived from digestible carbohydrates, more preferably 40 to 60%.

The present composition in the form of a tablet comprises fat. Preferably the fat of the present composition in the form of a tablet provides 35 to 60% of the total calories of the composition, preferably the fat provides 40 to 50% of the total calories. The present composition in the form of a tablet preferably comprises 10 to 40 wt. %, preferably 12.5 to 30 wt. % fat, more preferably 15 to 25 wt. % or more preferably 19 to 25 wt. %.

Preferably the fat comprises the essential fatty acids alpha-linolenic acid (ALA), linoleic acid (LA) and/or long chain polyunsaturated fatty acids (LC-PUFA). The LC-PUFA, LA and/or ALA may be provided as free fatty acids, in triglyceride form, in diglyceride form, in monoglyceride form, in phospholipid form, or as a mixture of one of more of the above. Preferably the present composition in the form of a tablet comprises at least one, preferably at least two lipid sources selected from the group consisting of rape seed oil (such as colza oil, low erucic acid rape seed oil and canola oil), high oleic sunflower oil, high oleic safflower oil, olive oil, marine oils, microbial oils, coconut oil, palm kernel oil and milk fat.

The present composition in the form of a tablet preferably comprises fat, protein and digestible carbohydrate in the ranges as described above. The present composition in the form of a tablet preferably comprises other fractions, such as vitamins, minerals, trace elements and other micronutrients in order to make it a complete nutritional composition. Preferably the composition in the form of a tablet is selected from the group consisting of an infant formula, follow on formula, toddler milk or formula and growing up milk, more preferably form the group consisting of an infant formula and follow on formula. Infant and follow on formulae comprise vitamins, minerals, trace elements and other micronutrients according to international directives.

Preferably the fat provides 35 to 60% of the total calories, the protein provides 5 to 15% of the total calories and the digestible carbohydrate provides 30 to 60% of the total calories of the composition in the form of a tablet. Preferably the present composition in the form of a tablet comprises lipid providing 40 to 50% of the total calories, protein providing 6 to 12% of the total calories and digestible carbohydrates providing 40 to 60% of the total calories of the composition. The amount of total calories is determined by the sum of calories derived from protein, lipids and digestible carbohydrates.

Preferably the composition in the form of a tablet according to the invention comprises between 7 and 25 wt % protein, 30 and 70 wt % carbohydrates and 10 and 30 wt % fat based on the total weight of the composition. Preferably the composition in the form of a tablet according to the invention comprises 8 to 10 wt % protein, 55 to 65 wt % carbohydrates, and 15 to 25 wt % fat based on the total weight of the composition.

Medical Food in Tablet Form

Another preferred embodiment is medical food in tablet form. Medical foods can be complete nutritional products comprising fat, carbohydrate, protein, and vitamins and minerals. Food supplements comprising ingredients in lower or imbalanced quantities are also part of the invention.

A specific problem related to medical foods is the relatively large quantities of unsaturated fatty acids they contain. These fatty acids are known to oxidize due to presence of oxygen in the composition and/or high temperatures necessary to sterilize the composition. Oxidation in general is a problem in the food industry determining to a large extent the shelf life of a product. Oxidation of poly-unsaturated fatty acids also diminishes the nutritional value of the fatty acids. It is known that oxidation of fatty acids produces free radicals, which are believed to play a role in the development of cancer and other degenerative diseases. The present inventors discovered that when nutritional products comprising fat wherein the fat comprises at least partly poly-unsaturated fatty acids such as linoleic acid, EPA, DHA or AA the oxidation of these fatty acids is largely prevented when the composition is in the tablet form. Therefore, a preferred composition in the form of a tablet according to the present invention comprises poly-unsaturated fatty acids (PUFA). Preferably the composition in the form of a tablet comprises at least 1 wt. % poly-unsaturated fatty acids. In particular EPA and DHA are very sensitive to oxidation. Therefore in a preferred embodiment according to the present invention the composition in the form of a tablet comprises at least 0.1 wt % EPA or DHA or a mixture thereof, based on the total weight of the composition, even more preferably between 0.1 and 5 wt % based on the total weight of the composition.

It has been found that the oxidation of PUFA becomes particularly a problem for the taste when at least 1 wt % of the fatty acids is present as EPA or DHA or a mixture thereof. Commercial preparations of EPA or DHA are often protected to oxidation by the addition of vitamin E. The fishy off-taste of nutritional products containing EPA or DHA is particularly bad when the composition contains more than about 1 wt % EPA or DHA based on the total dry weight of the composition. In a preferred embodiment according to the present invention of the composition in the form of a tablet therefore comprises protein, fat and carbohydrates wherein the fat comprises at least 1 wt % EPA or DHA or both based on the total weight of the composition, more preferably at least 1.2 wt % and even more preferably at least 1.5 wt % and preferably not more than 5 wt % EPA or DHA or a mixture thereof, based on total weight of the composition. When the tablet is coated, e.g. by film coating techniques known in the art, the penetration of oxygen from the air will likely further decrease, resulting in even less oxidation of the unsaturated fatty acids. Therefore in a preferred embodiment the composition in the form of a tablet according to the present invention is provided with a coating. Coatings that are suitable for nutritional tablets are known to the skilled person.

EXAMPLES

Example 1

In this example at a certain dissolving time the reconstitution of a composition in tablet form according to the invention (active) versus a control was measured The active was an Infant milk formula comprising 7.9 wt % dietary fiber, which was a mixture comprising galactooligosaccharides and long chain fructo oligosaccharides (GOS/IcFOS), and the control is the same formula wherein the GOS/IcFOS absent.

Tablets were prepared as follows. A die is placed on a weighing tool and placed on an analytical balance and a pre-determined amount of powder (active is 5.0 g, control 4.6 g) was weighted into the die. When enough powder was added, the lid of the die was placed on top of the die. The die was turned upside down and some pressure was applied to the puncher until the resistance of the powder was felt. The die was placed in a manual tablet press. The torch wrench was set onto the right amount of applied energy in Newton meters (Nm) and was placed on top of the manual tablet press. In this example the applied energy was 12 Newton meters. With the help of the torch wrench the puncher was lowered until the moment the pre-determined amount of energy was applied. The screw of the tablet press was turned in the opposite direction so the die could be removed. The die was turned upside down and the lid was removed. By pushing the piston inside the die the tablet was released.

The following method was used for determining the reconstitution:
- a bottle of 240 ml was filled with 90 ml water of 40° C.
- 3 tablets were placed in the bottle and the bottle was closed
- the bottle was placed in the bottle shaker and shaken for the indicated time (10-60 seconds)
- the content of the bottle was sieved over a sieve with a mesh size of 600 μm
- the milk was collected for further analysis
- the bottle was rinsed 2 times with 180 ml water of 40° C. and poured through the sieve, and the fluid that passed the sieve was discarded
- a picture was taken of every sieve Every sample was tested with water of 40° C. and with different shaking times, from 10 until 60 seconds. The collected (first) milk was used to determine the dry matter content.

Dry Matter:

The dry matter content was analysed with help of the "Monjonier" method. The reconstitution degree was calculated with the following formula:

Reconstitution (%)=(% dry matter content of sieved milk/% dry matter content of fully dispersed sample)*100.

FIG. 1 shows the influence of dietary fibres in tablets on reconstitution.

From the results it can be clearly seen that with a hardness between 15 N and 30 N as measured using a Schleuniger hardness tester and a force that was applied horizontally on the tablet with a constant test speed of 2 mm/s the tablets with the dietary fibers have a much shorter dissolving time and a better reconstitution than the composition without dietary fibers. A 95% reconstitution is regarded as sufficiently dissolved.

Example 2

Comparison of Medical Food Powders with and without Dietary Fibers on Reconstitution

| | | Medical powders Code | |
|---|---|---|---|
| Name | Unit | 120493 Nutrison - control | 120805 Nutrison MF - active |
| Nutrient (per 100 ml after dissolution) | | 100 ml | 100 ml |
| Energy (KJ) | kJ | 415 | 420 |
| Energy (kcal) | kcal | 99 | 100 |
| ProtEquiPD | g | 4.0 | 4..0 |
| Carbohydrate | g | 12.1 | 12.3 |
| Sugars | g | 1.9 | 1.9 |
| Glucose | g | 1.9 | 1..9 |
| Lactose | g | <0.03 | <0.03 |
| Maltose | g | 1.4 | 1.3 |
| PolySach | g | 10.0 | 10.1 |
| Starch | g | 0.0 | 0.2 |
| Fibre | g | 0.0 | 1.5 (7.5 wt %) |
| Soluble | g | 0.0 | 0.9 |
| Insoluble | g | 0.0 | 0.6 |
| Fat Total | g | 3.9 | 3.9 |
| Porosity (%) | | 77 | 73 |
| Reconstitution at 20 seconds | | 55% | 81% |

Tablets, prepared as described in example 1, wherein the food is a medical food. All ingredients were kept constant, except for the fibers. The hardness of the tablets was 16 N. The fibers in this composition comprise soy polysaccharides, resistant starch, inulin, Arabic gum cellulose and oligo fructose. As is clear from the result, the reconstitution at 20 seconds is much higher in the fiber containing product compared to the control product. Also at 60 seconds there was a relevant difference in reconstitution of 98% for the active and 91% for the control product.

Example 3

Comparison Between Infant Milk Formula with and without Galactooligosaccharides and Inulin on Reconstitution

| Name | | Control | Active |
|---|---|---|---|
| ProtEquiPD | g | 1.3 | 1.3 |
| Carbohydrate | g | 8.1 | 7.9 |

-continued

| Name | | Control | Active |
|---|---|---|---|
| Fibre | g | 0.0 | 0.62 (5 wt %) |
| Fat Total | g | 3.5 | 3.5 |
| Porosity | | 36 | 38 |
| Dissolution at 20 seconds | | 50% | 70% |

Tablets were prepared as described in example 1. The hardness of the tablets was between 15 and 16 N. In this example a particularly strong effect on dissolution was measured when comparing this infant formula with and without GOS/inulin. Also at 60 second, the dissolution of the active was 97% while the control was only 82%.

The invention claimed is:

1. A method for improving the dissolving time of a compressed powder composition comprising fat, protein and carbohydrates, the method comprising adding to the composition 1 to 15 wt % of the total weight of the composition at least one dietary fiber selected from the group consisting of galactooligosaccharides and long chain fructooligosaccharides.

2. The method according to claim 1, wherein the at least one dietary fiber is long chain fructooligosaccharides.

3. The method according to claim 2, wherein the dietary fiber comprises at least galactooligosaccharides.

4. The method according to claim 2, wherein the dietary fiber comprises a mixture of galactooligosaccharide and fructans.

5. The method according to claim 1, wherein the dissolving time is improved during preparation of a bottle.

6. The method according to claim 1, wherein the compressed powder composition dissolves for 95% in less than 35 seconds at 40 degrees Celsius.

7. The method according to claim 1, wherein the compressed powder composition comprises between 7 and 25 wt % protein, 30 and 70 wt % carbohydrates, 10 and 30 wt % fat based on the total weight of the composition.

8. The method according to claim 1, wherein the compressed powder composition comprises 8 to 10 wt % protein, 55 to 65 wt % carbohydrates, and 15 to 25 wt % fat based on the total weight of the composition.

9. The method according to claim 1, wherein the fat comprises poly-unsaturated fatty acids.

10. The method according to claim 9, wherein the fat comprises at least 1 wt % poly-unsaturated fatty acids based on the total weight of the composition.

11. The method according to claim 10, wherein the fat comprises at least 0.1 wt % EPA or DHA or a mixture thereof based on the total weight of the composition.

12. The method according to claim 11, wherein the fat comprises between 1 and 5 wt % EPA or DHA or a mixture thereof based on the total weight of the composition.

13. The method according to claim 1, wherein the dietary fiber consists of galactooligosaccharides and/or long chain fructooligosaccharides.

14. The method according to claim 1, wherein the compressed powder composition is an infant formula, a follow on formula, a toddler milk or formula or a growing up milk.

* * * * *